(12) United States Patent
McKay

(10) Patent No.: US 8,101,676 B2
(45) Date of Patent: Jan. 24, 2012

(54) OSTEOGENIC PASTE COMPOSITIONS AND USES THEREOF

(75) Inventor: William F. McKay, Memphis, TN (US)

(73) Assignee: Warsaw Orthopedic, Inc., Warsaw, ID (US)

( * ) Notice: Subject to any disclaimer, the term of this patent is extended or adjusted under 35 U.S.C. 154(b) by 1079 days.

(21) Appl. No.: 11/670,804

(22) Filed: Feb. 2, 2007

(65) Prior Publication Data

US 2007/0128249 A1 Jun. 7, 2007

Related U.S. Application Data

(63) Continuation of application No. 09/923,117, filed on Aug. 6, 2001, now Pat. No. 7,172,629.

(51) Int. Cl.
*A61L 24/00* (2006.01)
*A61F 2/00* (2006.01)
*C07K 14/51* (2006.01)

(52) U.S. Cl. ......... 523/116; 424/423; 424/602; 514/8.8; 514/16.7; 523/113; 523/114; 523/115

(58) Field of Classification Search .................. 523/113
See application file for complete search history.

(56) References Cited

U.S. PATENT DOCUMENTS

| | | | |
|---|---|---|---|
| 4,774,227 A | 9/1988 | Piez et al. | |
| 4,789,663 A | 12/1988 | Wallace et al. | |
| 4,795,467 A | 1/1989 | Piez et al. | |
| 4,888,366 A | 12/1989 | Chu et al. | |
| 5,024,841 A | 6/1991 | Chu et al. | |
| 5,035,715 A | 7/1991 | Smestad et al. | |
| 5,123,925 A | 6/1992 | Smestad et al. | |
| 5,204,382 A * | 4/1993 | Wallace et al. | 523/115 |
| 5,246,457 A | 9/1993 | Piez et al. | |
| 5,343,877 A * | 9/1994 | Park | 128/898 |
| 5,356,629 A | 10/1994 | Sander et al. | |
| 5,422,340 A * | 6/1995 | Ammann et al. | 424/489 |
| 5,425,770 A | 6/1995 | Piez et al. | |
| 5,507,813 A * | 4/1996 | Dowd et al. | 623/23.63 |
| 5,510,396 A * | 4/1996 | Prewett et al. | 523/113 |
| 5,626,861 A * | 5/1997 | Laurencin et al. | 424/426 |
| 5,646,129 A * | 7/1997 | Callegaro et al. | 514/54 |
| 5,674,292 A * | 10/1997 | Tucker et al. | 424/422 |
| 5,679,723 A | 10/1997 | Cooper et al. | |
| 5,693,615 A * | 12/1997 | Stone | 514/12 |
| 5,702,449 A * | 12/1997 | McKay | 623/17.16 |
| 5,739,286 A | 4/1998 | Silver et al. | |
| 5,752,974 A | 5/1998 | Rhee et al. | |
| 5,776,193 A | 7/1998 | Kwan et al. | |
| 5,854,207 A * | 12/1998 | Lee et al. | 514/2 |
| 5,976,234 A | 11/1999 | Chow et al. | |
| 5,977,204 A | 11/1999 | Niederauer et al. | |
| 6,187,047 B1 | 2/2001 | Kwan et al. | |
| 6,280,474 B1 | 8/2001 | Cassidy et al. | |
| 6,328,765 B1 | 12/2001 | Hardwick et al. | |
| 6,679,918 B1 | 1/2004 | Benedict et al. | |
| 2001/0014830 A1 | 8/2001 | Kwan et al. | |
| 2002/0076429 A1 | 6/2002 | Wironen et al. | |
| 2002/0082694 A1 | 6/2002 | McKay | |
| 2002/0183855 A1 | 12/2002 | Yammamoto et al. | |
| 2003/0236573 A1 | 12/2003 | Evans et al. | |
| 2004/0034434 A1 | 2/2004 | Evans et al. | |
| 2004/0064193 A1 | 4/2004 | Evans et al. | |
| 2004/0127987 A1 | 7/2004 | Evans et al. | |
| 2004/0138758 A1 | 7/2004 | Evans et al. | |
| 2004/0220680 A1 | 11/2004 | Yammamoto et al. | |

FOREIGN PATENT DOCUMENTS

| | | |
|---|---|---|
| EP | 0530804 | 3/1993 |
| WO | WO 89 04646 | 6/1989 |
| WO | WO 93 16657 | 9/1993 |
| WO | WO 96 39023 | 12/1996 |
| WO | WO 96 40297 | 12/1996 |
| WO | WO 97 40137 | 10/1997 |
| WO | WO 9740137 A1 * | 10/1997 |
| WO | WO 98 17330 | 4/1998 |
| WO | WO 98 40113 | 9/1998 |
| WO | WO 99 38543 | 8/1999 |

* cited by examiner

*Primary Examiner* — Mark Eashoo
*Assistant Examiner* — David Karst

(57) ABSTRACT

Described are osteogenic paste compositions with enhanced osteoinductive properties for use in bone repair. Compositions comprising a quickly resorbable paste carrier, a more slowly resorbed mineral matrix, and Bone Morphogenetic Protein (BMP) or other osteogenic factor are described which enable increased osteoinductive activity while retaining a reliable scaffold for the formation of new bone at the implant site. Methods for making and methods for therapeutic use of the compositions are also disclosed.

26 Claims, 2 Drawing Sheets

OSTEOGENIC PASTE COMPOSITIONS AND USES THEREOF

REFERENCE TO RELATED APPLICATION

This application is a continuation of U.S. application Ser. No. 09/923,117 filed Aug. 6, 2001 now U.S. Pat. No. 7,172,629 which claims the benefit of U.S. Patent Application Ser. No. 60/118,614 filed Feb. 4, 1999, both of which are hereby incorporated by reference in their entirety.

FIELD OF INVENTION

The present invention relates generally to osteogenic paste compositions containing a paste-form carrier and an osteogenic factor. In one specific aspect, this invention relates to osteogenic paste compositions containing a paste-form carrier, an osteogenic factor, and a substantial mineral component to provide a lasting scaffold for bone growth. This invention also relates to methods of making and using the osteogenic paste compositions.

BACKGROUND

As further background, bone grafting is commonly used to augment healing in the treatment of a broad range of musculoskeletal disorders. Grafting has been effective in reconstruction or replacement of bone defects, to augment fracture repair, to strengthen arthrodeses and to fill defects after treatment of tumors. Autograft techniques have been known for over 100 years and include the use of cortical and cancellous bone as grafting material. The use of autografts presents several serious drawbacks including the limited amount of potential donor material available, the requirement for two surgical intrusion sites on the patient, a high incidence of donor site morbidity, the tedious and complex nature of the techniques, particularly when vascularized grafts are involved, and the fact that donated bone can rarely be precisely sized or shaped to fit the needs of the implant site. Allografts can also be used in analogous procedures. Allografts have the benefits of avoiding two-site surgery on the patient and the elimination of donor site morbidity risk. However, allografts have increased risks of disease transmission and immunogenic implant rejection. Procedures used to reduce these new risks inherently decrease the viability of the allografts as effective implant material. Procedures with allografts also remain tedious and complex, suffer from limited source material and have the same limitations on sizing and shaping the implant to optimally fit the needs of the implant site.

A number of compositions have been developed to augment or replace autographic and allographic techniques to reduce or avoid the above mentioned drawbacks. Ceramics such as hydroxyapatite, tricalcium phosphate (TCP), and coralline hydroxyapatite have been shown to be beneficial osteoconductive matrices for use as fillers and/or expanders in bone graft material. Ceramics can add compression strength, but lack osteoinductive properties and, when used alone, lack shear and tensile strength. R. W. Bucholz, A. Carlson, R. E. Holmes, *Hydroxyapatite and tricalcium phosphate bone graft substitutes*. Orthop. Clin. North Am., Vol. 18(2), 1987, pg. 323-334 and R. W. Bucholz, A. Carlson, R. E. Holmes, *Interporous hydroxyapatite as a bone graft substitute in tibial plateau fractures*, Clin. Orthop., Vol. 240, 1989, pg. 53-62. Further, it has been shown in animal studies, that such ceramics can be filled with marrow to provide a beneficial level of initial progenitor cells and other osteogenic factors. H. Ohgushi, V. M. Goldberg, A. I. Caplan, *Heterotopic osteogenesis in porous ceramics induced by marrow cells*, J. Orthop. Res., Vol. 7, 1989, pg. 568-578.

The calcium phosphate based ceramics differ widely in their resorption characteristics once implanted. In addition to other factors, the resorption rate tends to increase with surface area of the ceramic, which in turn depends on the ceramic's particle shape, size, density and porosity. TCP is degraded 10-20 times faster than hydroxyapatite. Also partly as a result, if new bone development is established with a TCP implant, the TCP is generally remodeled better than hydroxyapatite in the final stage of bone formation. It is noteworthy that TCP is resorbed by osteoclast cells, whereas, the much slower resorption of hydroxyapatite is effected mainly by foreign-body giant cells. The giant cells have a limit as to the amount of hydroxyapatite they will resorb.

Pure ceramics do not offer optimum handling characteristics during implantation, but do offer excellent biocompatibility properties and tend to bond well to the existing bone. Ohgushi, et al. teaches the use of marrow infiltration of ceramics, while others have used various binders with granulated ceramics to formulate workable pastes that solidify to provide stable implants of desired shape and size. C. P. Desilets, L. J. Marden, A. L. Patterson and J. O. Hollinger, *Development of synthetic bone-repair materials for craniofacial reconstruction*, J. Craniofacial Surgery, Vol. 1(3), 1990, pg. 150-153.

Demineralized bone matrix (DBM) preparations have been researched extensively for use as bone implant material. DBM is prepared through the acid extraction of minerals from bone. It includes the collagen matrix of the bone together with acid insoluble proteins including bone morphogenic proteins (BMPs) and other growth factors. DBM can be processed as crushed granules, powder or chips. It can be formulated for use as granules, gels, sponge material or putty and can be freeze-dried for storage. Sterilization procedures required to protect from disease transmission may reduce the activity of beneficial growth factors in the DBM. DBM provides an initial osteoconductive matrix and exhibits a degree of osteoinductive potential, inducing the infiltration and differentiation of osteoprogenitor cells from the surrounding tissues. DBM lacks structural strength and is therefore only useful to fill well supported, stable skeletal defects such as cysts, simple fractures, and fillers for autographs and allographs. Examples of commercially available DBM products are Grafton® Allogenic Bone Matrix by Osteotech, Shrewbury, N.J., and Dynagraft® by Gensci Regeneration Laboratories, Irvine, Calif.

Various combinations of the above-mentioned bone implant materials have been made with a desire to obtain the benefits of the individual components without their individual drawbacks. Some combinations have met with a measure of success, but Y. Yamazaki, S. Shioda and S. Oida, *Experimental Study on the Osteo-Induction Ability of Calcium Phosphate Biomaterials with added Bone Morphogenic Protein*, Transaction of the Society for Biomaterials, 1986, pg. 111, teach that not all combinations of elements known to be individually beneficial for bone implant materials are additive in their beneficial characteristics or effective as composite implant materials. Yamazaki, et al. found that the osteoinductive potential of DBM and osteogenic protein extracts therefrom are inhibited by the addition of TCP or hydroxyapatite. No osteogenic composition has yet been found to be optimum in generalized usage and clinical results vary widely, even with seemingly well defined compositions. There remains a need for improved osteogenic implant materials that are consistently strongly osteoinductive, osteoconductive, easily workable in surgical procedures, and that provide strength and stability for new bone formation during the early stages of bone development, but are essentially completely incorporated and remodeled into bone by the end of the osteogenic process.

Compositions of mixed ceramics of TCP/hydroxyapatite and collagen are commercially available and can be enhanced by filling with autogenous bone marrow prior to implant. The composites are available as pastes or soft strips and tend to flow away from the implant site. The implant must therefore be carefully retained in place until the composite and any surrounding bleeding has fully clotted.

Compositions of bone gel known as GRAFTON® (see U.S. Pat. No. 5,481,601) comprising glycerol and DBM have been used singly and mixed with sand-like powder. Such compositions have been used to fill bone voids, cracks and cavities. GRAFTON® is available in flexible sheets or as a putty, thus making the composition more easily workable during implantation. Again, such compositions tend to flow away from the implant site.

Jefferies, in U.S. Pat. Nos. 4,394,370 and 4,472,840, teach a bone implant material composition of collagen and DBM or solubilized BMP that is optionally crosslinked with glutaraldehyde.

Caplan et al., in U.S. Pat. No. 4,620,327, describe the combination and partial immobilization by chemical cross-linking of soluble bone proteins with a number of solids to be implanted for bone repair/incorporation, including xenogenic bony implants, allografts, biodegradable masses and prosthetic devices to enhance new bone or cartilage formation. Ries et al., in U.S. Pat. No. 4,623,553, describe the glutaraldehyde or formaldehyde cross-linking of collagen and hydroxyapatite or TCP. Ries does not include any osteoinductive elements and is deemed only osteoconductive.

Some researchers have suggested the use of composites of TCP and/or biopolymers like polylactide, polyglycolide or their copolymers and particulate bone derivatives or BMP for craniofacial reconstruction. The TCP and biopolymers would provide a scaffold for new bone formation. The bone derivatives and BMP would induce osteogenesis beyond the slow, shallow osteoconduction induced by TCP and biopolymers alone. Desilets, et al.

Jefferies, in PCT WO 89/04646, describes osteoinductive implant materials having increased tensile strength by surface activating DBM or BMP with gluteraldehyde or other suitable cross-linking agent, followed by addition to a porous solid matrix where the activated DBM or BMP reacts with the solid to increase the cohesive strength of the composite. Jefferies also teaches the incorporation of therapeutic drugs into the matrix for the slow beneficial release thereof during the course of treatment.

In light of this background, there remain needs for improved osteogenic compositions and methods that effectively induce and support bone growth in mammals, including humans. The present invention is addressed to these needs.

SUMMARY OF THE INVENTION

The present invention generally provides osteogenic paste compositions including a paste-form carrier such as a gelatin paste and at least one osteogenic factor such as BMP-2 or another similar bone morphogenetic protein. A particular feature of the present invention relates to the discovery that the inclusion of an osteoblast- and osteoclast-stimulating osteogenic factor in a paste-form composition including a resorbable paste carrier causes a rapid and premature resorption of the carrier. This rapid resorption of the carrier can diminish or eliminate the capacity of the paste-form composition to effectively stimulate and support new bone formation in a void filled with the composition. This is particularly the case in primates, including humans, in which the rate of new bone formation is relatively slow.

Accordingly, one preferred embodiment of the present invention provides an osteogenic paste composition effective for the induction and support of new bone growth in a primate. The implant composition comprises a resorbable paste-form carrier, including for instance a paste made with a substance such as gelatin, hyaluronic acid, and/or carboxymethyl cellulose. The composition also includes an effective amount of an osteogenic factor, such as a bone morphogenetic protein, that stimulates both osteoblast cells and osteoclast cells. In addition, composition includes a substantial proportion of a particulate mineral that is effective to provide a scaffold for bone ingrowth when the resorbable paste carrier is resorbed at an increased rate due to the stimulation of osteoclast cell activity. Preferred such compositions of the invention are provided wherein the resorbable paste carrier includes gelatin, and/or wherein the resorbable paste carrier is flowable at temperatures above the body temperature of the mammal in which it is to be implanted, but transitions to a relatively non-flowable mass at or slightly above said body temperature.

Importantly, the particulate mineral matrix constitutes a substantial proportion of the paste composition as a whole, in order to provide an effective scaffold for bone ingrowth. In most cases, the particulate mineral have an average particle size between about 0.050 and about 5.0 mm, and will constitute about 20% to 80% by volume of the overall composition, more typically higher levels of about 40% to about 80% by volume. The particulate mineral can include, for example, a natural or synthetic mineral, e.g. a material selected from the group consisting of bone particles, Bioglass®, tricalcium phosphate, hydroxyapatite, biphasic calcium phosphate, corraline hydroxyapatite, biocompatible ceramic and non-resorbable biocompatible organic polymer. Biphasic calcium phosphate is a particularly preferred synthetic ceramic for use in the present invention, advantageously having a tricalcium phosphate:hydroyapatite weight ratio of about 80:20 to about 90:10.

In some preferred modes of carrying out the invention, the mineral comprises cancellous or cortical bone particles having an average particle size between about 0.050 and about 5.0 mm. Such bone particles can be of human or non-human (e.g. bovine) origin. In other modes, the mineral comprises tricalcium phosphate, biphasic calcium phosphate or hydroxyapatite having a particle size of about 0.50 to about 5.0 mm. In still another aspect of the invention, the paste composition further comprises demineralized bone matrix. The weight ratio of demineralized bone matrix to resorbable carrier is preferably between about 1:4 and about 3:2, respectively.

In one particularly preferred form of the present invention, an osteogenic paste composition for the induction of new bone growth in a primate is provided, comprising:

(a) a resorbable paste carrier comprising gelatin, the resorbable paste carrier formulated to be flowable at temperatures above the body temperature of the primate, and to transitions to a non-flowable mass at such body temperature;

(b) demineralized bone matrix;

(c) a bone morphogenic protein that stimulates osteoblasts and osteoclasts, more preferably BMP-2 or BMP-7; and (d) cortical or cancellous bone particles, having an average particle size of between about 0.050 and about 5.0 mm, and constituting about 20% to about 80% by volume of the overall implant composition.

Still other preferred embodiments of the present invention provide methods for treating bone trauma, defect or disease, or for effecting artificial arthrodeses in a mammal, comprising the step of implanting an osteogenic paste composition of the invention in a primate at a site of desired new bone formation.

The present invention provides an improved osteogenic implant material that is strongly osteoinductive and that can be formed into precise shapes either prior to implant or during the surgical procedure itself. The present invention also provides implant materials that retain stable shapes at the implant site and do not deform, migrate, or flow away from the implant site before ossification is established. Significantly, the present invention also provides advantageous implant materials that have enhanced osteoinductive potential and provide a matrix that is workable during implantation, but not resorbed prior to the establishment of bone within the void to be filled. Such preferred compositions provide a mineral scaffold for the generation of new bone that is subsequently incorporated into the bone matrix as the new bone matures. The invention also provides methods for preparing such compositions and of using such compositions to treat bone trauma, disease and defects, wherever osteogenesis is desired. These and other objects, features and advantages of the present invention will be readily apparent from the following description.

DESCRIPTION OF THE PREFERRED EMBODIMENTS

Figure 1:
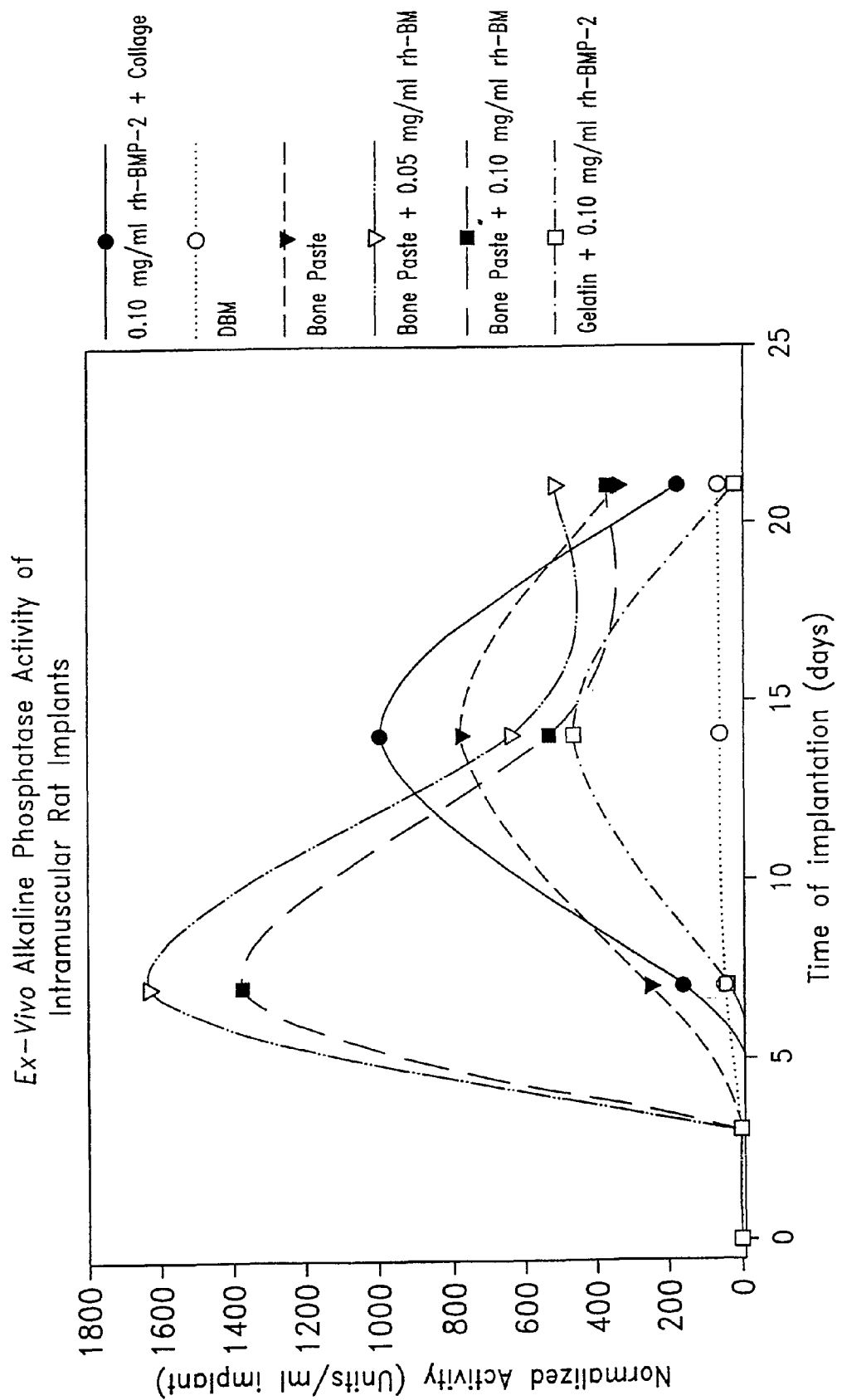
FIG. 1 shows ex vivo alkaline phosphatase activity as a function of time for intramuscular rat implants of demineralized bone matrix, a paste of gelatin and demineralized bone matrix, and of rhBMP-2 in each of a collagen sponge, a paste of gelatin and demineralized bone matrix, and in a paste of gelatin alone.

For the purpose of promoting an understanding of the principles of the invention, reference will now be made to certain embodiments thereof and specific language will be used to describe the same. It will nevertheless be understood that no limitation of the scope of the invention is thereby intended, such alterations, further modifications and applications of the principles of the invention as illustrated herein being contemplated as would normally occur to one skilled in the art to which the invention relates.

As indicated above, the present invention generally provides osteogenic paste compositions including a paste-form carrier and a bone-growth-inducing amount of an osteogenic factor such as a bone morphogenetic protein (BMP). The present invention features osteogenic paste compositions effective for use in primates, wherein the compositions exhibit high osteoinductive potential and provide a lasting mineral scaffold to support bone ingrowth. Such preferred compositions include a resorbable paste-form carrier, for example an aqueous paste including gelatin, and an osteogenic factor that stimulates the action of both osteoblasts (which biologically facilitate the formation of bone) and osteoclasts (which biologically facilitate the resorption of bone). In accordance with the present invention, it has been found that the incorporation of effective inductive amounts of such osteogenic factors, for example bone morphogenetic proteins, stimulates osteoclasts to such a level that the resorbable carrier is too quickly resorbed and, in the absence of a high mineral component in the composition, causes the performance of the composition to suffer in some cases to the extent that the observance of substantial bone ingrowth is sporadic.

Accordingly, a feature of the present invention is the provision of a paste-form osteogenic composition that includes a substantial amount of a relatively slowly-resorbed mineral component that remains at the implant site after the carrier has been rapidly resorbed, in order to provide a scaffold for new bone formation that is not prematurely resorbed due to the osteoclastic potentiation by the bone morphogenic protein in the composition. The present invention also provides methods for using such osteogenic compositions in treatment of bone trauma, disease and defects, for artificial arthrodeses and for other treatment where new bone formation is desired, especially in primates, including humans.

Generally speaking, compositions in accordance with the present invention are in paste form and comprise a resorbable carrier, especially a gelatin paste, and an osteogenic factor such as a BMP that stimulates osteoblasts and osteoclasts, e.g. BMP-2 or BMP-7, especially BMP-2. The preferred compositions of the invention also include a substantial proportion (i.e. at least about 20% by volume) of a particulate, porous mineral matrix dispersed within the carrier. Such compositions can also include other resorbable components, for example demineralized bone matrix.

As to the carrier, in accordance with the present invention, it will be biologically resorbable and will contribute to providing a paste form to the composition allowing its implantation and retention at the candidate site for bone ingrowth. Preferred carriers will include resorbable macromolecules from biological or synthetic sources, for example gelatin, hyaluronic acid carboxymethyl cellulose, collagen, peptides, and the like. In more preferred inventive forms, the resorbable carrier, especially gelatin, is formulated into the composition such that the composition is flowable at temperatures above the body temperature of the mammal into which the material is to be implanted, but transitions to be relatively non-flowable at or slightly above such body temperature. The resorbable carrier may be formulated into the composition so the flowable state is a liquid or a flowable gel, and the non-flowable state is a stable gel or solid. In certain embodiments of the invention, the resorbable carrier is gelatin derived from the species receiving the implant, while in others the gelatin is derived from a species other than that of the mammal receiving the implant.

As is well known, when gelatin is solubilized in warm or hot aqueous solutions, the molecules have little organization. However, as a gelatin solution is allowed to cool, the gelatin molecules intertwine into a three dimensional matrix and the viscosity of the solution increases. At a characteristic set temperature, a phase transformation changes the flowable solution into a non-flowable gel. The set time, set temperature and density of the resulting non-flowable mass are dependent on several factors including the concentration of gelatin, the molecular weight and the intrinsic viscosity of the gelatin molecules and on the pH of the composition. Other components of the composition can affect the set time and temperature as well. The shortest set times are typically at the isoelectric point of the gelatin molecules.

As indicated in the passages above, other carriers can be used instead of or in addition to gelatin, to provide the paste composition. Illustrative macromolecules for these purposes include, for example, hyaluronic acid, cellulose derivatives such as carboxymethyl cellulose, collagens, peptides and the like. These and other similar materials which function as resorbable thickening agents will be suitable, and their incorporation into compositions of the present invention will be within the purview of those ordinarily skilled in the field given the teachings herein.

Paste compositions of the invention may also include other potentially osteoinductive substances, including for example demineralized bone matrix (DBM). As is known in the field, DBM can be prepared by acid demineralization of bone and when so prepared contains, among other constituents, the collagen matrix of the bone and acid insoluble proteins. DBM has been shown previously to be mildly osteoinductive by itself and has a favorable porous matrix for the ingrowth of bone. Methods of producing DBM are known in the art and are, therefore not elaborated upon here (see for example U.S. Pat. No. 5,405,390, herein incorporated by reference for this purpose). In a preferred form, DBM having a particle size of between about 0.10 and about 1.00 mm will be incorporated within compositions of the present invention. The DBM can be derived from the same or a different mammalian species as that in which the implant material is to be used. When used, the DBM is preferably blended with the resorbable carrier in a weight ratio between about 1:4 and about 3:2 DBM to resorbable carrier. Commercially available preparations of DBM are suitable for use in the present invention provided they may be uniformly blended with the other elements of the composition.

As indicated above, preferred paste compositions of the invention also include an osteoinductive factor, such as an osteoinductive protein or a nucleotide sequence encoding an osteoinductive protein operably associated with a promoter (e.g. provided in a vector such as a viral vector), for example a bone morphogenetic protein or a gene encoding the same operationally associated with a promoter which drives expression of the gene in the animal recipient to produce an effective amount of the protein. The bone morphogenic protein (BMP) in accordance with this invention is any BMP able to stimulate differentiation and function of osteoblasts and osteoclasts. Examples of such BMPs are BMP-2, BMP-4, and BMP-7, more preferably rhBMP-2 or rhBMP-7, most preferably, rhBMP-2. Purified recombinant BMPs are preferred for use in the inventive compositions for their provision of high osteoinductive potentials. BMP gene sequences and methods for producing recombinant and naturally-derived BMPs are known in the art, and for additional information on this subject reference may be made, for instance, to U.S. Pat. Nos. 5,108,753; 5,187,076; 5,366,875; 4,877,864; 5,108,922; 5,116,738; 5,013,649; 5,106,748; and 4,294,753; and International Publication Nos. WO93/00432; WO94/26893; and WO94/26892. The osteoinductive factor may also be LIM mineralization protein (LMP) or a suitable vector incorporating a gene encoding the same operably associated with a promotor, as described in WO99/06563 (see also genbank accession No. AF095585). When such vectors are employed as osteogenic factors in accordance with the invention, they are preferably delivered in conjunction with cells, for example autologous cells from the recipient of the implant. Most preferably the vector is delivered in conjunction with autologous white blood cells derived from bone marrow or peripheral blood of the recipient.

The osteogenic factor will be incorporated in an amount which is effective to stimulate the formation of bone within the animal recipient. In more preferred compositions incorporating protein osteogenic factors, the osteogenic factor will be incorporated in a weight ratio of about 1:100 to about 1:1000 relative to the overall composition, more preferably about 1:100 to about 1:500. As will be understood, when the osteogenic factor comprises a nucleotide sequence, sufficient amounts of the delivery vehicle (vector) will be incorporated to cause significant transduction of cells, so as to cause the generation of sufficient protein at the site to induce bone formation.

The osteogenic factor may be incorporated into the paste in any suitable manner, for example by pre-impregnating the mineral particles with the osteogenic factor prior to blending with the paste carrier, by blending the factor with the carrier, or both. Alternatively or in addition, amounts of the osteogenic factor can be blended with the carrier/mineral mixture immediately prior to implantation.

The porous mineral used in accordance with the preferred embodiments of the present invention includes a natural or synthetic mineral that is effective to provide a scaffold for bone ingrowth as the resorbable carrier and other more rapidly resorbed elements of the implant composition are resorbed. Illustratively, the mineral matrix may be selected from one or more materials from the group consisting of bone particles, Bioglass®, tricalcium phosphate, biphasic calcium phosphate, hydroxyapatite, corraline hydroxyapatite, and biocompatible ceramics. Biphasic calcium phosphate is a particularly preferred synthetic ceramic for use in the invention. Desirably, such biphasic calcium phosphate with have a tricalcium phosphate:hydroxyapatite weight ratio of about 50:50 to about 95:5, more preferably about 70:30 to about 95:5, even more preferably about 80:20 to about 90:10, and most preferably about 85:15.

In another preferred aspect of the invention, the mineral matrix includes bone particles, possibly cancellous but preferably cortical, ground to provide an average particle diameter between about 0.050 and 5.0 mm. Both human and non-human sources of bone are suitable for use in the instant invention, and the bone may be autographic, allographic or xenographic in nature relative to the mammal to receive the implant. Appropriate pre-treatments known in the art may be used to minimize the risks of disease transmission and/or immunogenic reaction when using bone particles in the mineral matrix.

In one embodiment of the instant invention, xenogenic bone that has been pretreated to reduce or remove its immunogenicity is used to provide the porous mineral matrix in the implant composition. For example, calcining or deproteinizing of the bone can be used to reduce the risks of immunogenic reactions to the implant material.

The level at which the mineral is incorporated into the preferred mineral-enhanced compositions of the invention is important to the provision of beneficial osteoinductive properties to the compositions. In general, the minimum level of mineral is dependent on activity of the BMP in the composition; the higher the activity of the BMP, the greater the content of the mineral matrix required to counter the osteoclastic potentiation of the BMP. As the BMP concentration increases, so does the rate of resorption of the resorbable carrier and DBM if present. As a result, the mineral content must be sufficient to provide a scaffold for the ingrowth of new bone while not abrogating the structural integrity of the composition. The mineral should also be such that as the new bone matures, the mineral is made an integral part of the tissue matrix or is resorbed during remodeling of the new bone in the natural course of bone growth and development.

In a preferred form of the invention, the mineral constitutes about 20% to about 80% by volume of the composition, more preferably about 40% to about 80%. Generally speaking, the amount of mineral in the paste composition will be sufficient to provide a scaffold that will remain in the patient for a period of time sufficient for the formation of osteoid in the area for which bone growth is desired. Typically, this period of time will be about 6 to about 8 weeks.

As further enhancements of the compositions of the present invention, those skilled in the art will readily appreciate that other osteogenic enhancing factors may be incorporated into the composition. Such additional factors include, but are not limited to host compatible osteogenic progenitor cells, autographic bone marrow, allographic bone marrow, transforming growth factor-beta, fibroblast growth factor, platlet derived growth factor, insulin-like growth factor, microglobulin-beta, antibiotics, antifungal agents, wetting agents, glycerol, steroids and non-steroidal anti-inflammatory compounds.

In use, the paste-form implant compositions of the invention are implanted at a site at which bone growth is desired, e.g. to treat a disease, defect or location of trauma, and/or to promote artificial arthrodesis. The paste form of the compositions enables their positioning, shaping and/or molding within voids, defects or other areas in which new bone growth is desired. In the case of implant compositions which are flowable at temperatures higher than the body temperature of the mammal in which they are to be implanted, yet which transition to a non-flowable mass at or near such body temperature, the composition is heated to a temperature at which it is flowable, but which will not denature any osteogenic factor present; molded or otherwise shaped to the shape of the desired new bone; cooled to a temperature sufficient to transition the osteogenic implant material into a non-flowable mass either in situ or implanted at the site of desired new bone formation after setting up. In other preferred situations, the paste composition does not require heating to above body temperature (about 37° C.) for flowability, for example wherein the paste composition is flowable at temperatures below 37° C. and cures or solidifies into a non-flowable mass upon heating or upon contact with a separate curing agent. Such cases are particularly advantageous in that heat-induced denaturation of the osteogenic factor is less of a concern.

Once in place, the paste form implant compositions of the invention will effectively induce and support the ingrowth of bone into the desired area even in a primate subject such as a human exhibiting a relatively slow rate of bone formation compared to smaller mammals, for example rodents or rabbits. In particular, while the paste carrier is generally resorbed relatively quickly, the substantial mineral component remains as a scaffolding to support new bone growth in and through the desired area. In this regard, it is preferred that the mineral matrix be chosen and included in an amount which will provide a scaffold which is detectable in the treated subject for a period sufficient for the formation of osteoid in the volume to be filled with bone, typically about 6 to about 8 weeks. This will facilitate effective bone formation even where the resorbable carrier and other quickly-resorbed components of the paste are rapidly eliminated from the implant site.

Compositions of the invention are especially advantageous when used in bones or bone portions that are vascularized to only moderate or low levels. These areas present particularly low rates of bone formation, and as such the rapid resorption of the carrier poses enhanced difficulties. Examples of moderate or only slightly vascularized sites include, for example, transverse processes or other posterior elements of the spine, the diaphysis of long bones, in particular the mid diaphysis of the tibia, and cranial defects An especially preferred use of paste compositions of the invention is as an implant to promote arthrodesis between vertebrae in spinal fusions in humans or other primates, including for example interbody, posterior and/or posterolateral fusion techniques. Although the rate of bone formation in the primate spine is relatively slow overall and thus will benefit generally from the present invention, the elements to be fused in posterior and posterolateral fusions exhibit particularly low levels of vascularization and thus fusions of these elements are expected to benefit markedly from the invention. In addition, in accordance with other aspects of the invention, the osteogenic paste compositions of the invention can be incorporated in, on or around a load-bearing (e.g. having a compressive strength of at least about 10000 N) implant device such as a fusion cage, dowel, or other device having a pocket, chamber or other cavity for containing an osteogenic composition, and used in a spinal fusion such as an interbody fusion.

The invention will now be more particularly described with reference to the following specific Examples. It will be understood that these Examples are illustrative and not limiting of the invention.

Example 1

Rat Study Comparing the Effect of rhBMP-2 on Osteogenic Capacity of a Matrix Consisting of Collagen Derived Gelatin and Demineralized Bone Matrix (DBM).

Thirty young adult male Sprague-Dawley rats weighing between 200-220 g, were randomly assigned to two groups. Each animal was surgically implanted with six 0.050 mL samples. The samples were inserted in pockets incised into the rectus abdominus muscles on either side of the midline. Samples were placed three to a side, evenly spaced in lines extending from below the sternum to above the mid-groin.

Two of the six samples for each animal were positive controls, one being DBM alone, the second being Helistat® Absorbable Collagen Sponge (ACS) onto which 0.004 mg rhBMP-2 had been adsorbed. Group I animals were also given duplicate samples of a gelatin/DBM injectable matrix (Gelatin Bone Paste) and duplicate samples of the Gelatin Bone Paste mixed with 0.001 mg rhBMP-2. Group II animals were given duplicate samples of the Gelatin Bone Paste mixed with 0.002 mg rhBMP-2 and duplicate samples of the gelatin without DBM (Gelatin) mixed with 0.002 mg rhBMP-2.

Five animals from each group were sacrificed at each time point of two, fourteen and twenty-one days. At sacrifice, the implant areas were excised and analyzed for alkaline phosphatase activity, radiography, bone density, histology and histomorphometry.

FIG. 1 shows alkaline phosphatase activity in the samples. Increased activity is indicative of infiltration of the implants by osteoprogenitor cells. The timing and magnitude of increased activity is evidence of the osteoinductive potential of the implant. The Gelatin Bone Paste samples with rhBMP-2 exhibited earlier and higher alkaline phosphatase activity peaks than the controls or the Gelatin Bone Paste alone. Surprisingly, the 0.001 mg rhBMP-2 samples gave higher activity peaks than did the 0.002 mg rhBMP-2 samples.

Figure 2:
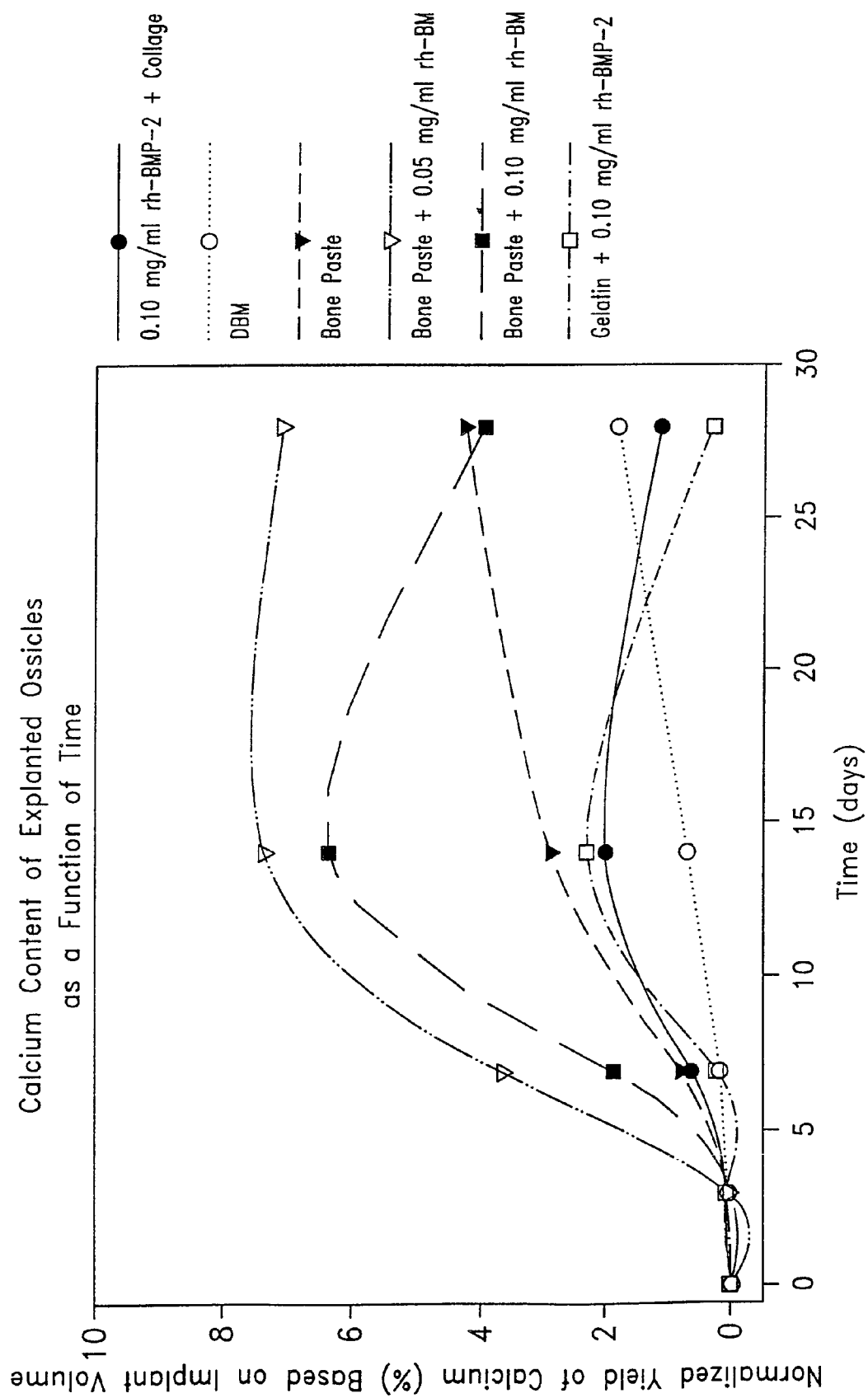
FIG. 2 shows calcium content of explanted ossicles as a function of time for intramuscular rat implants of demineralized bone matrix, a paste of gelatin and demineralized bone matrix, and of rhBMP-2 in each of a collagen sponge, a paste of gelatin and demineralized bone matrix, and in a paste of gelatin alone.

FIG. 2 shows the calcium content of the excised implants. Increased calcium content is indicative of bone formation. As with the alkaline phosphatase data, the Gelatin Bone Paste samples with rhBMP-2 out-performed both the controls and the Gelatin Bone Paste without rhBMP-2 samples in initiating calcification of the implant. It is again surprising that the 0.001 mg rhBMP-2 in Gelatin Bone Paste samples were more effective at initiating calcification than the 0.002 mg rhBMP-2 in Gelatin Bone Paste samples. It is also noteworthy that the twenty-one day samples of the higher concentration of rhBMP-2 showed a diminishing of calcification compared to the fourteen day samples.

These data are indicative of the osteoclastic potentiation of rhBMP-2 balancing its osteoblast stimulating properties; higher rhBMP-2 concentrations stimulate the resorption of the essentially collagen matrix, limiting the osteogenic potential of such matrices that do not incorporate mineral matrix elements to provide prolonged scaffolding for the bone formation process. It should be noted that the ACS controls containing 0.004 mg rhBMP-2 and the gelatin samples containing 0.002 mg rhBMP-2 had the most readily resorbable matrices and gave the poorest calcification performances for samples containing rhBMP-2. See FIG. 2.

Example 2

Monkey Study Comparing Osteogenicity of rhBMP-2 Containing Implant Matrices.

Studies in a monkey spinal fusion model were conducted to determine the effectiveness of three paste compositions. The compositions were the gelatin bone paste of Example 1, that paste containing autograft bone chips, and that paste containing rhBMP-2 at a single level of the spine. Each composition was used in bilateral fusion of vertebra in rhesus monkeys and analyzed for its ability to induce new bone formation. In doing so, CT scans were taken every two months over a six-month period. The results demonstrated variable bone growth in monkeys receiving the paste of Example 1 alone and in the paste containing autograft bone chips, but no growth in monkeys receiving the paste and rhBMP-2. This observation is expected to be due to the premature resorption of the carrier in the rhBMP-2-containing paste, leaving no matrix for bone ingrowth. Accordingly, incorporation of a substantial mineral component in a BMP-containing paste in accordance with the present invention will provide a lasting matrix and scaffold for bone ingrowth, thus improving performance.

The invention has been described above in detail, with specific reference to its preferred embodiments. It will be understood, however, that a variety of modifications and additions can be made to the procedures disclosed without departing from the spirit and scope of the invention. Such modifications and additions are desired to be protected. In addition, all publications cited herein are indicative of the level of skill in the relevant art, and are each hereby incorporated by reference each in their entirety as if individually incorporated by reference and fully set forth.

What is claimed is:

1. An osteogenic paste composition effective for the induction of new bone growth in a primate, comprising:
   a resorbable paste carrier comprising a macromolecular carrier material;
   demineralized bone matrix, wherein the demineralized bone matrix contains particles with a particle size of between about 0.10 and 1.00 mm, wherein the ratio of demineralized bone matrix to resorbable paste carrier is between about 1:4 and about 3:2 by weight;
   an osteogenic factor incorporated into the paste composition to stimulate osteoclasts to cause an increase in a rate of resorption of the macromolecular carrier material, when the paste is implanted in the primate; and
   a porous particulate mineral comprising tricalcium phosphate and hydroxyapatite in a weight ratio of tricalcium phosphate:hydroxyapatite of about 70:30 to about 95:5, the porous particulate mineral in an amount of at least 20% by volume of the composition, said amount being effective to provide a scaffold for bone ingrowth as the resorbable paste carrier is resorbed.

2. The composition of claim 1, wherein the composition comprises 5-45% by weight resorbable carrier.

3. The composition of claim 1 wherein the resorbable carrier is flowable at temperatures above the body temperature of the mammal, but transitions to a non-flowable mass at or slightly above said body temperature.

4. The composition of claim 1 wherein the mineral has an average particle diameter of about 0.050 to about 5.0 mm.

5. The composition of claim 1 wherein the mineral comprises mammalian bone particles having a particle size of about 0.050 to about 5.0 mm.

6. The composition of claim 1 wherein the mineral comprises cortical human bone particles having an average particle diameter of about 0.050 to about 5.0 mm.

7. The composition of claim 1 wherein the osteogenic factor comprises a bone morphogenic protein selected from BMP-2, BMP-4, BMP-6 or BMP-7, a LIM mineralization protein, or a nucleotide sequence encoding said bone morphogenic protein or LIM mineralization protein.

8. The composition of claim 1 further comprising one or more osteogenic enhancing factors selected from the group consisting of osteogenic progenitor cells, autographic bone marrow, allographic bone marrow, transforming growth factor-beta, fibroblast growth factor, platlet derived growth factor, insulin-like growth factor, microglobulin-beta, antibiotics, antifungal agents, wetting agents, glycerol, steroids and non-steroidal anti-inflammatory compounds.

9. The composition of claim 1 wherein the mineral constitutes about 20% to about 80% by volume of the composition.

10. A method for inducing bone growth in a primate, comprising implanting in the primate a composition according to claim 1, at a site at which bone growth is desired.

11. The method of claim 10, wherein the site is in the spine of the primate.

12. The method of claim 11, which is a spinal fusion.

13. The method of claim 12, wherein the spinal fusion is an interbody spinal fusion.

14. The method of claim 12, which is a posterolateral spinal fusion.

15. The method of claim 12, wherein the fusion includes a fusion between transverse processes of adjacent vertebrae.

16. The method of claim 11, wherein the primate is a human.

17. A method of performing a spinal fusion in a human, comprising implanting between adjacent vertebrae to be fused an effective amount of a composition according to claim 1.

18. The method of claim 17, wherein the composition is implanted in combination with a load bearing device.

19. A method for inducing bone growth in a primate, comprising: heating an effective amount of the osteogenic paste composition of claim 1 to a temperature at which it is flowable; implanting said osteogenic paste composition at a site of desired new bone formation; and cooling the osteogenic paste composition to a temperature sufficient to transition the osteogenic paste composition to a non-flowable mass.

20. The method of claim 19 wherein the implant material further comprises demineralized bone matrix.

21. The method of claim 19 wherein the primate is a human.

22. An osteogenic implant composition effective for the induction of new bone growth in a mammal, comprising:
   a resorbable paste carrier comprising gelatin and hyaluronic acid, the resorbable carrier formulated to be flowable at temperatures above the body temperature of the mammal, and to transition to a non-flowable mass at said body temperature;

demineralized bone matrix, wherein the ratio of demineralized bone matrix to resorbable paste carrier is between about 1:4 and about 3:2 by weight;

an osteogenic factor incorporated into the paste carrier in an amount to stimulate osteoclasts to cause an increase in a rate of resorption of the composition when the composition is implanted in the mammal; and a particulate mineral having an average particle size of about 0.050 to about 5.0 mm, said mineral constituting at least 20% by volume of said composition and comprising tricalcium phosphate and hydroxyapatite in a weight ratio of tricalcium phosphate:hydroxyapatite of about 70:30 to about 95:5.

23. The composition of claim 22 wherein the mineral constitutes about 20% to about 80% by volume of the composition.

24. The composition of claim 22 wherein the mineral comprises human bone particles.

25. The composition of claim 22 wherein the mineral comprises non-human bone particles, said particles having been treated to reduce their immunogenicity in humans.

26. The composition of claim 22 wherein the osteogenic factor is a bone morphogenic protein selected from BMP-2, BMP-4, BMP-6 and BMP-7, a LIM mineralization protein, or a nucleotide sequence encoding said bone morphogenic protein or LIM mineralization protein.

* * * * *

UNITED STATES PATENT AND TRADEMARK OFFICE
CERTIFICATE OF CORRECTION

Page 1 of 1

PATENT NO. : 8,101,676 B2
APPLICATION NO. : 11/670804
DATED : January 24, 2012
INVENTOR(S) : McKay It is certified that error appears in the above-identified patent and that said Letters Patent is hereby corrected as shown below:

On the Title Page, in Field (73), under "Assignee", in Column 1, Line 1, delete "ID" and insert -- IN --, therefor.

Signed and Sealed this
First Day of May, 2012

David J. Kappos
*Director of the United States Patent and Trademark Office*